US008864923B1

(12) United States Patent
Stiles et al.

(10) Patent No.: US 8,864,923 B1
(45) Date of Patent: Oct. 21, 2014

(54) BALLISTIC MODIFIER FORMULATION FOR DOUBLE BASE PROPELLANT

(75) Inventors: Stephen N. Stiles, Port Tobacco, MD (US); Paul R. McCool, Waldorf, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 2044 days.

(21) Appl. No.: 11/342,941

(22) Filed: Jan. 30, 2006

(51) Int. Cl.
*C06B 25/30* (2006.01)
*C06B 23/00* (2006.01)
*C06B 25/18* (2006.01)
*G01N 33/22* (2006.01)

(52) U.S. Cl.
CPC .............. *C06B 25/18* (2013.01); *G01N 33/222* (2013.01)
USPC ... 149/19.8; 149/19.93; 149/19.7; 149/19.92; 149/109.6

(58) Field of Classification Search
USPC .............. 149/19.6, 19.43, 19.7, 19.92, 109.6
See application file for complete search history.

(56) References Cited

U.S. PATENT DOCUMENTS

| | | | |
|---|---|---|---|
| 3,951,704 A | 4/1976 | Stack | 149/19.8 |
| 3,954,667 A | 5/1976 | Stack | 556/28 |
| 4,420,350 A | 12/1983 | Camp et al. | 149/98 |
| 4,462,848 A | 7/1984 | Elrick | 149/19.92 |
| 4,521,261 A | 6/1985 | Davies | 149/92 |
| 5,254,186 A | 10/1993 | Downes et al. | 149/19.4 |
| 5,385,619 A | 1/1995 | Downes et al. | 149/19.4 |
| 5,639,987 A | 6/1997 | Berteleau et al. | 149/19.8 |
| 5,652,409 A | 7/1997 | Thompson et al. | 149/98 |
| 6,024,810 A | 2/2000 | Neidert et al. | 149/19.8 |
| 6,692,655 B1 * | 2/2004 | Martins et al. | 252/183 |

OTHER PUBLICATIONS

"NSWCIHD-AA-16 and NSWCIHD-AA-17 Extuded Double Base (EDB) Process Development and Performance of Ballisic Modifiers," S.N. Stiles and P.R. McCool, Mar. 25-28, 2003, VA.
"NSWCIHD-AA-16 and NSWCIHD-AA-17 Extuded Double Base (EDB) Process Development and Performance of Ballisic Modifiers," S.N. Stiles and P.R. McCool. Presentation; 2003, VA.
Department of Defense Directive, No. 5230.24, "Distribution Statements on Technical Documents," Mar. 18, 1987.
Department of Defense, "Distribution Statements on Technical Documents-Extracts from DOD Directives 5230.24," printed on Jan. 18, 2006.
U.S. Appl. No. 11/345,682, filed Jan. 30, 2006, Stiles, et al.

* cited by examiner

*Primary Examiner* — Carol M Koslow
(74) *Attorney, Agent, or Firm* — Fredric J. Zimmerman

(57) ABSTRACT

A double base propellant modifier uses a combination of a lead component, a tin component and a copper component in physical contact to effect super-rate burning of double base propellants with defined plateau and mesa burning rate characteristics.

8 Claims, 1 Drawing Sheet

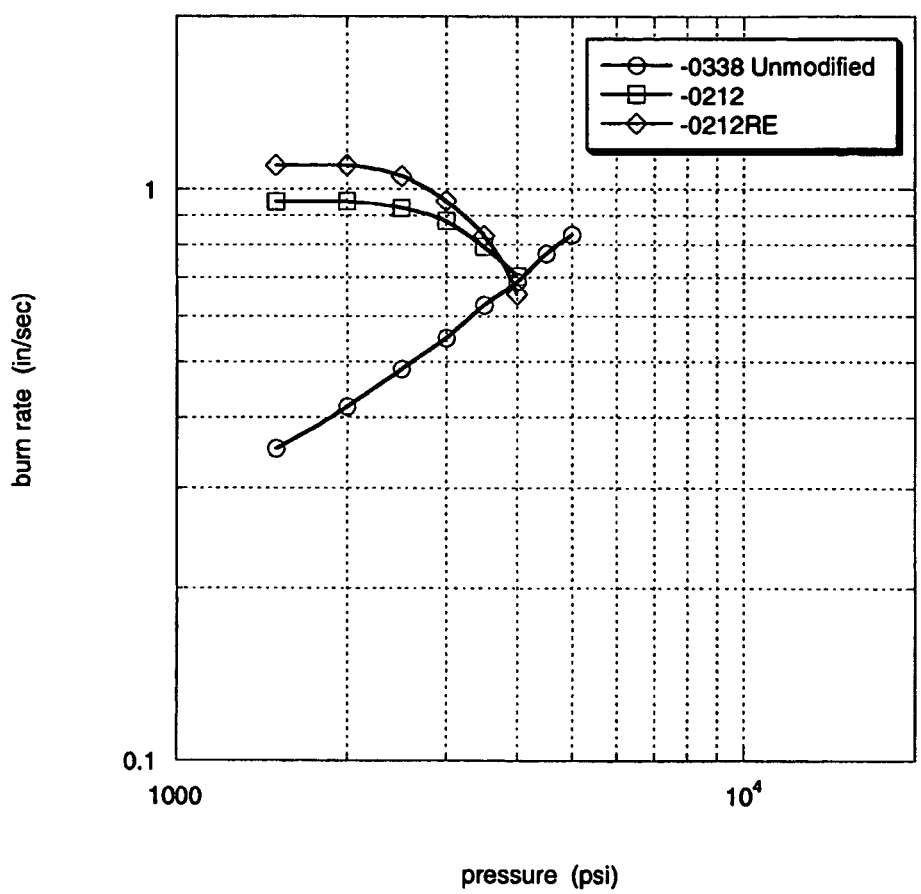

BALLISTIC MODIFIER FORMULATION FOR DOUBLE BASE PROPELLANT

STATEMENT REGARDING FEDERALLY SPONSORED RESEARCH OR DEVELOPMENT

The invention described herein may be manufactured and used by or for the Government of the United States of America for governmental purposes without the payment of any royalties thereon or therefore.

FIELD OF THE INVENTION

Modifier formulations for double base propellants are used to effect super-rate burning of the double base propellants with defined plateau and mesa burning rate characteristics.

BACKGROUND

Ballistic modifiers for double base propellants are used to modify burning characteristics of double base propellants. A double base propellant generally contains an energetic polymer, such as nitrocellulose, plasticized into a gel by an energetic plasticizer, such as nitroglycerine. Additives may be included in these double base propellants to improve the mechanical or ballistic properties of the propellant. One such additive is termed a ballistic modifier, which alters the inherently high dependence of the burning rate on chamber temperature and chamber pressure.

The objective in ballistic modification of double base rocket propellants is to obtain plateau or mesa burning over a desired range of pressure and burning rate levels. These terms come from the shape of a log-log plot of the burning rate equation for double-base propellants which is given as: $r=CP^n$ or $\log r = n \log P + \log C$, where r is the burning rate, P is the combustion chamber pressure, C is a constant for each propellant composition at any one temperature, and n is a constant for non-modified propellants but is a variable in modified propellants. In plateau- or mesa-burning propellants, "n" varies from very high positive values to zero or low negative values. Thus, a plot of log r against log P would give a straight line with a slope of "n" for a non-modified propellant, whereas a "plateau" shaped line or a mesa-shaped line exists for modified propellants. The performance of a ballistic modifier is measured in terms of the rate increase and pressure extent of plateau burning. Super rate defines the concept of substantially increasing burn-rate at any given pressure over burn-rates obtained from non-modified propellants.

There is a need in the art to provide improved modifiers for double base propellants. The present invention addresses this and other needs.

SUMMARY OF THE INVENTION

The present invention includes a double base propellant modifier having a combination of a lead component, a tin component and a copper component.

The present invention also includes a process for defining plateau and mesa burning rate characteristics of a double base propellant by integrating the above-described double base propellant modifier into a double base propellant that is ignited.

DETAILED DESCRIPTION OF THE DRAWINGS

FIG. 1 illustrates a comparison of unmodified and modified propellant mixes.

DETAILED DESCRIPTION OF AN EMBODIMENT OF THE INVENTION

The present invention includes modifier formulations used to effect super-rate burning of double base propellants with defined plateau and mesa burning rate characteristics. These modifiers are particularly useful in solid rocket propellants. The double base propellant modifier of the present invention includes a combination of a lead component, a tin component and a copper component. It has been discovered that the incorporation of lead, tin and copper modifier components provides unique advantages in controlling these parameters. In particular, a mixture of lead oxide (PbO), tin oxide ($SnO_2$) and cupric oxide (CuO) can be used to achieve super-rate, plateau and mesa burning rate characteristics. The three components are separate, chemical molecular components, that is, separate molecules, but are physically combined, or in combination, by being in intimate, immediate physical contact with each other, that is, substantially adjacent to each other, and impart synergistic properties of the combination of the three component once the modifier components are incorporated into the double base propellant.

Propellants of the present invention may include energetic polymers and combinations of energetic polymers known in double base propellants, such as, plastic bonded explosives, such as, nitroguanidine, aromatic nitramines, such as, tetryl, ethylene dinitramine, nitrate esters, such as, nitroglycerine, butanetriol trinitrate and PETN (pentaerythritol tetranitrate), other nitroaromatic compounds, such as, trinitrotoluene (TNT) triaminobenzene (TATB) triaminotrinitro benzene (TATNB) and hexanitrostilbene, nitroglycerine, nitrocellulose, etc., alicylclic nitramines, such as, RDX (1,3,5-cyclotrimethylene-2,4,6,-trinitramine) and HMX (1,3,5,7-cyclotetramethylene-2,4,6,8-tetranitramine) and TATND (tetranitrotetraminodecalin) and combinations and mixtures thereof, and the like, including plasticized fibers thereof, energetics, such as, GAP (glycidyl azide polymer), BDNPA/F (bis-2-dinitropropylacetral/formal), bis-(2-fluoro-2,2-dinitroethyl) formal, diethylene glycol dinitrate, glycerol trinitrate, glycol trinitrate, triethylene glycerol dinitrate, trimethylolethane trinitrate butanetriol trinitrate, or 1,2,4-butanetriol trinitrate, may be included. Examples of suitable energetic binder materials are nitrocellulose, polyvinyl nitrate, nitroethylene, nitroallyl acetate, nitroethyl acrylate, nitroethyl methacrylate, trinitroethyl acrylate, dinitropropyl acrylate, C-nitropolystyrene and its derivatives, polyurethanes with aliphatic C- and N-nitro groups, polyesters made from dinitrocarboxylic acids and dinitrotrodiols and nitrated polybutadienes.

The lead component of the present invention may include elemental lead or lead of various oxidative states. Representative examples of the lead component include Pb, PbO, $PbO_2$, $Pb_3O_4$ and combinations thereof. An embodiment includes PbO. The lead component modifier may be present in amounts from about 0.25 wt % to about 0.45 wt %. Representative particle sizes for the lead component range from about 1-micron to about 100-micron, and more particularly, from about 1-micron to about 20-microns in size. The tin component of the present invention may include elemental tin or oxidated tin compounds. Representative examples of the tin component include Sn, SnO, $SnO_2$ and combinations thereof. An exemplary embodiment includes $SnO_2$. The tin component modifier may be present in amounts from about 0.15 wt % to about 0.35 wt %. Representative particle sizes for the tin component range from about 1-micron to about 100-microns, and more particularly from about 1-micron to about 20-microns in size. Additionally in the present invention, the copper component may include elemental lead or copper of various oxidative states. Representative examples of the lead component include Cu, CuO, $Cu_2O$ and combinations thereof. An embodiment includes CuO. The copper component modifier may be present in amounts from about 1.6 wt % to about 2.3 wt %. Representative particle sizes for the copper component range from about 1-micron to about 100-microns, and more particularly from about 1-micron to about 10-microns in size. The lead, tin and copper components are milled to specified parameters to provide definitive plateau and mesa burning characteristics for a given double base propellant. Accordingly, various defined plateau and mesa burning characteristics may be achieved with modification of the particle size and/or mount of each of the individual modifier components.

In an embodiment, mixtures of lead oxide (PbO), tin oxide ($SnO_2$) and cupric oxide (CuO) are particularly useful in modifying super-rate, plateau and mesa ballistic characteristics. As seen in FIG. 1, this combination of these three components provides a super-rate, plateau and mesa ballistic (SBR) characteristics in the double base propellants. Referring to FIG. 1, a comparison of unmodified and modified propellant mixes is shown combined in plasticized nitrocellulose fibers. Mix-0338 represents the burn rate as a factor of pressure for an unmodified composition of plasticized nitrocellulose fibers. Mix-0212 represents the burn rate as a factor of pressure for an modified composition of plasticized nitrocellulose fibers with the addition of PbO, $SnO_2$ and CuO. Mix-0212RE represents the burn rate as a factor of pressure for the same composition as mix 0212 with the addition of twenty more passes on the even speed roll mill. As seen in the graph of FIG. 1, the combination of the lead, tin and copper provides controllable plateau and mesa ballistic characteristics. The ballistic modifiers lead oxide (PbO), tin oxide ($SnO_2$) and cupric oxide effect super rate, plateau and mesa burning when in intimate contact with each other and the plasticized nitrocellulose fibers. Substitution of these compounds with the same metal-based compound of different oxidative states, e.g., replacing lead oxide (PbO) with $PbO_2$, $Pb_3O_4$ or Pb, tin oxide ($SnO_2$) with SnO or Sn and the cupric oxide (CuO) with $Cu_2O$ or Cu may be used to effect super rate, plateau and mesa burning. The changes in ballistic modifier composition would expect to alter strand burn rate profile shown in FIG. 1, while producing characteristic super-rate, plateau and mesa ballistic characteristics.

The new modifier formulation of the present invention achieves super-rate, plateau and mesa ballistic (SBR) characteristics in double base propellants. In an embodiment, the new formulation is lead oxide (PbO), tin oxide ($SnO_2$) and cupric oxide (CuO). The plateau and mesa burning rate characteristics of a double base propellant are defined by the double base propellant modifier with the integration of the modifier into the double base propellent, which is then burned.

Representative manufacture of the modified propellant includes achieving the desired burning rate characteristics in part by using a water slurry premixing process. The three component modifiers are added, in a wet state, to wet paste during a mixing process. Modified propellant paste batches are aged up to 120 days and dried to a minimum of twelve percent moisture content. The modified paste is processed on a heated differential roll mill for approximately three minutes, after which final burning rate characteristics are achieved by additional processing on the even speed roll mill. Alternatively, processing the propellant by adding ballistic modifiers, in a dry state, to wet paste during a mixing process. The modified propellant paste batches are dried down to one percent or less moisture content. The dry paste is processed on an even speed roll mill with up to forty passes. However, this second method of processing leads to an increase in roll mill fires because of the dry state of the propellant paste and the amount of work being induced on the roll mills. Pre-processing of the ballistic modifiers provides increased control over the final burning rate characteristics.

EXPERIMENTAL (ACTUAL) RESULTS

A double base propellant modifier may be produced through a water slurry premixing process. 8.8 g of PbO, 5.94 g of $SnO_2$ and 45.36 g of CuO, in the wet state, may be added to a wet paste having 2,268 g of plasticized nitrocellulose fibers, during a mixing process. The resultant modified propellant paste may be placed in batches and aged up to 120 days and dried to a minimum of twelve percent moisture content. The dried paste may be processed on a heated differential roll mill for approximately three minutes, followed by processing on a heated even speed roll mill. Final burning rate characteristics may be achieved by additional processing of the even speed roll mill.

The modifier of the present invention may be useful in propellants for military Propulsion Actuated Devices (PAD), such as, those devices used in United States Navy Aircrew Escape Systems in aircraft, such as, the F/A-18, F-14, T-45A, EA-6B and T-6A, or programs under the NACES Preplanned Product Improvement Effort and the NASA T-38 Escape System Upgrade.

The foregoing summary, description, and examples of the present invention are not intended to be limiting, but are only exemplary of the inventive features, which are defined in the claims.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What is claimed is:

1. A double base propellant modifier system, comprising:
a lead component;
a tin component;
a copper component; and
plasticized nitrocellulose fibers being combined with the lead component, the tin component and the copper component.

2. The double base propellant modifier system of claim 1, wherein the lead component is selected from at least one of Pb, PbO, $PbO_2$, and $Pb_3O_4$.

3. The double base propellant modifier system of claim 1, wherein the lead component is comprised of PbO.

4. The double base propellant modifier system of claim 1, wherein the tin component is selected from at least one of Sn, SnO, and $SnO_2$.

5. The double base propellant modifier system of claim 1, wherein the tin component is comprised of $SnO_2$.

6. The double base propellant modifier system of claim 1, wherein the copper component is selected from at least one Cu, CuO, and $Cu_2O$.

7. The double base propellant modifier system of claim 1, wherein the copper component is comprised of CuO.

8. The double base propellant modifier system of claim 1, wherein the lead component comprises PbO, the tin component comprises $SnO_2$ and the copper component comprises CuO.

\* \* \* \* \*